United States Patent
Goldsmith et al.

(10) Patent No.: US 6,436,057 B1
(45) Date of Patent: Aug. 20, 2002

(54) METHOD AND APPARATUS FOR COUGH SOUND ANALYSIS

(75) Inventors: William T. Goldsmith, Masontown; David Frazer, Fairmont; Jeffrey Reynolds, Morgantown; Aliakbar Afshari, Morgantown; Kimberly Friend, Morgantown; Walter McKinney, Morgantown, all of WV (US)

(73) Assignee: The United States of America as represented by the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 09/556,196

(22) Filed: Apr. 21, 2000

Related U.S. Application Data

(60) Provisional application No. 60/130,864, filed on Apr. 22, 1999.

(51) Int. Cl.[7] ................................. A61B 7/00
(52) U.S. Cl. ..................... 600/586; 600/52 J
(58) Field of Search ................. 600/586, 590, 600/529–543

(56) References Cited

U.S. PATENT DOCUMENTS 4,254,302 A * 3/1981 Walshe ...................... 381/67
4,463,764 A * 8/1984 Anderson et al. ........... 600/532

OTHER PUBLICATIONS

Goldsmith, W. T, et al., "Frequency Time and Energy Analysis of Cough Sounds", ECTB, HELD, and CIB, DRDRS, National Institute for Occupational Safety and Health, and Pulmonary and Critical Care Medicine, WVU School of Medicine, Morgantown, WV 26505. Presented at International Lung Sounds Conference Oct. 1998 in Boston, MA. Also published in proceedings.

Frazer, D. G., et al., "Analysis of Cough Sounds as an Index of Lung Disease", PPRB, HELD and CIB, DRDS, National Institute for Occupational Safety and Health, and Pulmonary and Critical Care Medicine, WVU School of Medicine, Morgantown, WV 26505. Presented at the American Thoracic Society Meeting, Mar. 1998. Also published in proceedings.

Friend, K. A., "Wavelet Analysis and Morphology for the Detection of Wheeze in Cough Sounds", Engineering and Control Technology Branch, Health Effects Laboratory Division, National Institute for Occupational Safety and Health, Morgantown, WV. Presented at the Biosignal Interpretation Workshop, Apr. 1999 In Chicago. Also published in proceedings.

(List continued on next page.)

*Primary Examiner*—Kevin Shaver
*Assistant Examiner*—Pamela L. Wingood
(74) *Attorney, Agent, or Firm*—Klarquist Sparkman, LLP

(57) ABSTRACT

A fast, simple, and reliable method and apparatus for recording cough sounds for diagnosing pulmonary disorders and diseases is provided. This method uses signal analysis techniques to extract quantitative information from recorded cough sound pressure waves. The generated data can be used to diagnose pulmonary disorders and diseases as well as track the effectiveness of treatment regimes over time. The method can also be used to quickly and reliably screen individuals at risk of pulmonary disorders and diseases. A system according to one embodiment includes a mouthpiece connected to the proximal end of a tube. The distal end of the tube is connected to a flexible tube. A microphone is attached to the tube between the distal and proximal ends therof for recording sound pressure waves. A calculated cough sound index (CSI) can be used in diagnostic applications.

26 Claims, 9 Drawing Sheets

OTHER PUBLICATIONS

Goldsmith, W. T., "A System for Recording High Fidelity Cough Sound Measurements", Engineering and Control Technology Branch, National Institute for Occupational Safety and Health, Morgantown WV., Presented at the Biosignal Interpretation Workshop Apr. 1999 in Chicago. Also published in proceedings.

Thorpe, C. W., et al., "Towards a quantitative description of asthmatic cough sounds", *Eur Respir J.*, 1992, 5, 685–692.

Debreczeni, L. A., et al., "Spectral Analysis of Cough Sounds Recorded With and Without a Nose Clip", *Bull Eur. Physiopathol. Respir.*, No. 10, pp. 57s–61s.

Oppenheim, A. V., et al. "The Speech Model, In: Discrete–time signal processing" New Jersey, Prentice Hall, Chapter 12, pp 816–825.

Debreczeni, L. A., et al., "Spectra of the Voluntary First Cough Sounds", *Acta Physiologica Hungarica vol. 75,* (2), pp. 117–131 (1990).

Yanagihara, N., et al., "The Physical Parameters of Cough: the Larynx in a Normal Single Cough", *Acta. Oto–laryngol.*, 61: 495–510. (1965).

Piiria, P., et al., "Differences in Acoustic and Dynamic Characteristics of Spontaneous Cough in Pulmonary Diseases", *Chest* 96:46–53. (Jul. 1989).

Kendel, M.G. et al., 1952, The Advanced theory of Statistics, vol. 1, Distribution Theory, New York, Hafner.

Leith, D. E., et al., 1987, "Cough, In: The handbook of Physiology, the Respiratory System", edited by A. Fishman, P. t. Macklem and J. Mead, Bethesda, MD, *Am. Physiological Society,* Sec. (3). chapter 20, 315–336.

Sears, F. W., et al., 1956 Rotation In: University Physics, Massachusetts, Addison–Wesley Publishing Company, Inc., Chapter 9, 157–180. (Not Available).

Troop, L. J., et al., (1989), Cough sound analysis: A new tool for the diagnosis of asthma? *Family Pract.,* 6(2): 83–85.

Troop, L. J., et al., 1990, A portable system for the spectral analysis of cough sounds in asthma, *J. of Asthma,* 27 (6) 393–397.

* cited by examiner

METHOD AND APPARATUS FOR COUGH SOUND ANALYSIS

RELATED APPLICATION

This application is based on, and claims benefit of, U.S. Provisional Application Ser. No. 60/130,864 filed on Apr. 22, 1999.

FIELD OF THE INVENTION

This invention relates to methods and apparatuses for the analysis of patient's coughs. More specifically, this invention relates to methods and apparatuses for the analysis of patient's coughs to aid in diagnosing pulmonary disorders and diseases. This method uses signal analysis techniques to extract quantitative information from recorded cough sound pressure waves. Moreover, the method allows the recordation of cough sound waves while avoiding distortions caused by reflections. The generated data can be used to diagnose pulmonary disorders and diseases as well as track the effectiveness of treatment regimes over time. The method can also be used for screening the general population, or populations at higher risk, so that such pulmonary disorders and diseases can be detected as early as possible so that appropriate treatment can be started as soon as possible.

BACKGROUND OF THE INVENTION

Cough is associated with well over 100 different pulmonary diseases and is one of the most common signs or symptoms of respiratory disease. Even though cough may be an unwanted complication of a pulmonary disease, it has often been used by physicians as an effective diagnostic tool. Since cough sounds are composed of acoustic information which can be altered by lung disease and since cough has essentially the same acoustical characteristics whether performed voluntarily or involuntarily, analysis of voluntary cough sounds has the potential to become a useful noninvasive tool for screening large populations of workers to evaluate their pulmonary function. The use of cough sound analysis to aid in the identification of lung disease has several distinct advantages since testing can be quickly and easily administered while requiring only a minimum amount of technician or patient training.

In order to describe the events that occur during a cough, physiologists have subdivided a cough into 4 different phases (Leith et al., Cough, In: *The Handbook of Physiology, The Respiratory System* edited by A. Fishman, P. T. Macklem and J. Mead, Bethesda, Md., Am. Physiological Society, Sec(3) Chapter 20, 315–336 (1987)). During the initial phase, called the inspiration phase, a variable volume of air is inhaled into the lungs. The second phase, referred to as the compression phase, begins as the glottis closes and the muscles of expiration begin to contract increasing thoracic pressure. The third phase is called the expulsion phase. At the start of the third phase, the glottis opens and gas flows rapidly from the lung. During the fourth and final phase, called the cessation phase, muscle activity is reduced and airflow is diminished.

The physical characteristics of a cough are illustrated in FIG. 1. Flow from the mouth during a cough is shown in FIG. 1A. Positive values represent flow from the lungs while negative flow values indicate air flow into the lungs. During the initial phase of a cough (phase I) air flow is negative as air enters the lungs. The volume of air inspired is variable and is said to be a function of the anticipated forcefulness of the cough (Yanagihara et al., "The Physical Parameters of Cough: the Larynx in a Normal Single Cough," *Acta. Oto-laryngol.* 61: 495–510 (1966)). As compression of air occurs during phase II of the cough, the glottis closes and airflow ceases. When the glottis reopens, in approximately 200 ms, flow initially increases and then decreases rapidly creating a flow transient. This initial rapid change in flow during phase III is referred to as supramaximal flow and is thought to result from the air rapidly leaving the flexible airway system as the airways compress during the initial part of the expulsion phase of a cough. At the same time that air is leaving the airways during the initial portion of phase III, expiratory flow from the lung periphery rises sharply to maximal flow which is limited by the maximum expiratory flow-volume relationship that is unique for each lung. Air flow leaving the lungs during a cough, therefore, is a summation of the transient air leaving the airways at a supramaximal flow rate and the air leaving the periphery of the lungs at maximal flow. During the cessation phase IV of a cough, airflow from the lungs diminishes and then approaches zero as muscle activity decreases.

FIG. 1B illustrates a typical sound pressure wave generated by a cough. It has been suggested that the cough sounds are generated during phase III and sometimes during phase IV of a cough. The cough sound, itself, can be subdivided into two and sometimes three parts (Thorpe et al., "Towards a Quantitative Description of Asthmatic Cough Sounds," *Eur. Respir. J.* 5: 685–692 (1992)). The first part of a cough sound is referred to as the initial burst and represents the sound transient that is associated with the glottis opening. The second or middle part corresponds to the interval of near steady, maximal flow coming from the periphery of the lung which occurs with the glottis maximally open. The third part of a cough, called the final burst, is not always present, but is believed to occur in some subjects who close their glottis during the cessation phase of a cough.

Airflow from the lung during a cough and the maximum expiratory flow volume (MEFV) relationship of a lung have much in common. During a forced expiration the airways, which are very flexible cylindrical structures, undergo compression and decrease in cross-sectional area as air rapidly passes through them. As a result, one or more choke points is created in the airway system during maximal gas flow. After a choke point has formed, flow from the lungs becomes independent of the driving pressure. This is important because it implies that airflow through the airway system should become effort independent during the performance of a MEFV maneuver. Once effort independence is reached, the MEFV relationship becomes repeatable. Flow-volume curves recorded during a MEFV maneuver define the limits of flow and volume that can be achieved during most expiratory maneuvers in a given individual. Leith et al. (1987) have stated that a surprisingly modest expiratory effort is required to reach the outer limits of the flow-volume domain for a given individual, making forced expiration a reliable pulmonary function test. FIG. 2 shows an example of an MEFV curve while expiring with a maximum effort into a spirometer. An example of the flow volume relationship of a lung during a cough is superimposed on the MEFV curve in FIG. 3. During the initial phase of a cough, air is inspired into the lungs. This is indicated by the increase in lung volume as the operating point on the flow-volume curve moves to the left throughout phase I. During the compression phase, there is no gas flow so phase II is represented by a single point on the diagram. During the initial part of phase III, a supramaximal flow transient is observed as the volume of air in the flexible airways decreases quickly as the airways begin to collapse. Following the very brief flow transient, maximal flow is achieved which approaches the maximal flow reached during the performance of a MEFV maneuver. The events that occur during this portion of the cough are very similar to those that occur during a MEFV maneuver; therefore, it can be assumed that airflow leaving the lung during a cough reaches flow limitation and is reasonably reproducible when successive coughs are performed beginning at the same lung volume. Since the mechanisms producing cough sounds are dependent upon air flow, it seems likely that cough sounds are also reproducible if similar lung histories are followed prior to each cough.

A block diagram of a simple model illustrating how cough sounds are produced is shown in FIG. 4. It is thought that the acceleration and turbulence of air within the airways caused by the rapid expulsion of air from the lungs generates band limited noise which is then modified by the resonances of the lungs' upper airways and possibly the oral and nasal cavities as air travels toward the mouth. Peaks that occur in the spectra of cough sounds result from resonances along the cough sound pathway, and they are similar to the formants observed in speech analysis. A second source of sound is referred to as a wheeze and is thought to result from the fluttering of airway walls as gas moves rapidly through the airways. A similar model has previously been proposed for the study of unvoiced speech (Oppenheim et al., "The Speech Model" in *Discrete-time Signal Processing*, New Jersey, Prentice Hall, Chapter 12, 816–825 (1989)).

In the past, several groups of investigators have recorded cough sounds in a variety of ways and have attempted to develop a technique which could be used to show differences in cough sounds between healthy subjects and those with respiratory diseases. It was thought that any substantial differences between coughs could eventually become useful in identifying persons with respiratory diseases. These initial studies examined the coughs of subjects with a variety of obstructive lung diseases, but the most often studied population was those having asthma.

Debreczeni et al. ("Spectral Analysis of Cough Sounds Recorded with and Without a Nose Clip," *Bull. Eur. Phys-iopathol. Respir. Suppl.* No. 10, 57s–61s (1987); "Spectra of the Voluntary First Cough Sound," *Acta Physiol. Hung.* 75(2): 117–131 (1990)) recorded sound pressure waves and computed the average spectra of cough sounds from patients with several types of obstructive lung disease. The spectra were used to determine how cough sound energy was distributed within several frequency bands and to distinguish between coughs from healthy subjects and those subjects with lung disease.

Piirila et al. ("Differences in Acoustic and Dynamic Characteristics of Spontaneous Cough in Pulmonary Diseases," *Chest* 96: 46–53 (1989)) recorded cough sound pressure waves and airflow for a sequence of coughs and then computed average cough spectra. The peak values representative of the dominant frequency components within the cough were extracted for comparison. Spectrograms were also computed and the length of the cough maneuver was measured by determining the time that sound energy had a frequency component present at 500 Hz. They reported that cough sound duration was longer for asthmatic coughs than for coughs from control subjects. One problem with interpreting these studies, however, is that sequences of coughs were studied instead of single coughs. As a result, it has been difficult to interpret the measurements and conclusions of this study concerning the duration of a cough.

Researchers have studied several aspects of recording and interpreting cough sounds. Initially, waterfall plots of cough spectrograms were examined to determine if there were differences in cough sounds of children with asthma before and after exercise (Toop et Al., "Cough Sound Analysis: A New Tool For the Diagnosis of Asthma?", *Family Pract.*, 6(2): 83–85 (1989)). More recently, attempts have been made to evaluate cough sounds using more quantitative methods so that meaningful comparisons could be made between cough sounds of selected individuals (Thorpe et al., "Towards a Quantitative Description of Asthmatic Cough Sounds," *Eur. Respir. J.* 5: 685–692 (1992)). The cough sound was divided into two or three parts and the characteristics of each part was studied independently. Power spectra were computed, normalized, and treated as histograms. The mean frequency, standard deviation, skewness, and kurtosis were calculated. In addition, the energy within selected frequency bands was examined and differences in coughs from persons with several types of obstructive lung disease were noted. This study also examined features of the sound pressure wave with respect to time including the duration, root mean square (RMS) value and zero crossing rate. Interestingly, no significant difference in the total duration of a cough between healthy subjects and those with obstructive lung diseases was reported. They did note, however, that both the duration of the initial burst and zero crossing rates of the cough waveform during each of the first two phases were smaller for asthmatic than for non-asthmatic coughs.

A variety of methods have been used to record and digitize cough sounds for analysis. The methods that have been used, however, have a large influence on the quality of the signal used for the acoustical analysis. Debreczeii, et al. (1987, 1990) recorded cough sounds of a seated subject in a quiet room with a microphone directed towards the subject's mouth from a distance of 50 cm. Sounds were recorded on an analog tape recorder and then digitized at a rate of 5 kHz and 20 kHz. Piirila et al. (1989) recorded cough sounds from subjects in a sitting position with a microphone attached to the skin of their chest wall located over the sternal manubrium. The sounds were recorded with a tape recorder; the bandwidth of their spectral analysis was 9 kHz. Toop et al. ("A portable system for the spectral analysis of cough sounds in asthma," *J. of Asthma* 27(6) 393–397 (1990)) described the design of a system used to record cough sounds. A patient coughed into a tube with a pneumotach and microphone attached. The cough signal was digitized at 5 kHz for analysis with a personal computer which limited the bandwidth of their analysis to frequencies below 2.5 kHz. Since the pneumotach modified the characteristics of the sound pressure wave reaching the microphone, these investigators estimated the correct acoustical response by deconvolving their average spectral measurements by Weiner filtering.

In spite of past efforts, it would be desirable to provide a simple, reliable, and fast diagnostic method to analyze coughs in order to assist physicians in diagnosing lung disorders or diseases. It is also desirable to provide a simple, reliable, and fast diagnostic method to analyze coughs which will allow physicians to monitor the effectiveness of treatments prescribed for lung disorders or diseases. It is also desirable to provide a simple, reliable, and fast diagnostic method to analyze coughs which can be used to screen populations for lung disorders or diseases, especially in cases where such lung disorders or diseases can be detected in an early stage where treatments can be more effectively administered and damage to lung function can be avoided or minimized. The methods and apparatuses of this invention provide such diagnostic methods.

SUMMARY OF THE INVENTION

This invention provides a fast, simple, reliable method and apparatus for recording cough sounds for diagnostic and other medical purposes. More specifically, this invention relates to methods and apparatuses for the analysis of patient coughs to aid in diagnosing pulmonary disorders and diseases. This method uses signal analysis techniques to extract quantitative information from recorded cough sound pressure waves. The generated data can be used to diagnose pulmonary disorders and diseases as well as track the effectiveness of treatment regimes over time. The method can also be used to quickly and reliably screen individuals at risk of pulmonary disorders and diseases. The discovery of early stages of pulmonary disorders or diseases may allow earlier treatment and/or environmental modification to reduce the risk of irreversible injury to pulmonary function.

The present invention provides a method for analyzing coughs for diagnostic purposes. This invention also provides a system for recording high fidelity cough sound measurements. Moreover, this invention provides a simple, non-invasive system that can quickly and easily be administered with minimum technician and patient training. The system comprises a mouthpiece, a tube having a distal end and a proximal end, a flexible tubing having a distal end and a proximal end, and a microphone; wherein the mouthpiece is attached to the proximal end of the tube, wherein the distal end of the tube is attached to the proximal end of the flexible tube, wherein the microphone is attached to the tube between its distal and proximal ends such that the microphone can record sound pressure waves within the system without distorting the pressure waves, and wherein the flexible tubing is sufficiently long so there are essentially no reflected sound pressure waves which interfere with the recording of the sound pressure waves at the microphone. Preferably, the system also includes a computer system to assist in recording and analyzing the sound pressure waves. Preferably, the distal end of the flexible tubing has an anechoic termination to further reduced or attenuate reflected sound waves.

This invention also provides a method for analyzing a patient's cough for diagnostic purposes, said method comprises (1) providing a system for analyzing coughs wherein the system comprises a mouthpiece, a tube having a distal end and a proximal end, a flexible tubing having a distal end and a proximal end, and a microphone; wherein the mouthpiece is attached to the proximal end of the tube, wherein the distal end of the tube is attached to the proximal end of the flexible tube, wherein the microphone is attached to the tube between its distal and proximal ends such that the microphone can record sound pressure waves within the system without distorting the pressure waves, and wherein the flexible tubing is sufficiently long so there are essentially no reflected sound pressure waves which interfere with the recording of the sound pressure waves at the microphone; (2) allowing the patient to cough into the mouthpiece; (3) recording the sound pressure waves generated by the patient's cough with the microphone; and (4) analyzing the recorded sound pressure waves. Preferably, the recorded sound pressure waves are digitized and then analyzed. Preferably, the recorded sound pressure waves are analyzed using spectrograms from which contour plots can be generated.

These and other objectives and advantages of the present invention will be apparent to those of ordinary skill in the art upon consideration of the present specification.

BRIEF DESCRIPTION OF THE DRAWINGS

FIG. 7 provides the frequency content of the cough on the vertical axis versus time on the horizontal axis; amplitude or intensity of individual frequency components are plotted on a logarithmic scale using the color scale on the right hand side of the Figure. FIG. 8 provides the same data in a waterfall type plot where the spectral intensity is plotted on a logarithmic scale.

DESCRIPTION OF THE PREFERRED EMBODIMENTS

Figure 5:
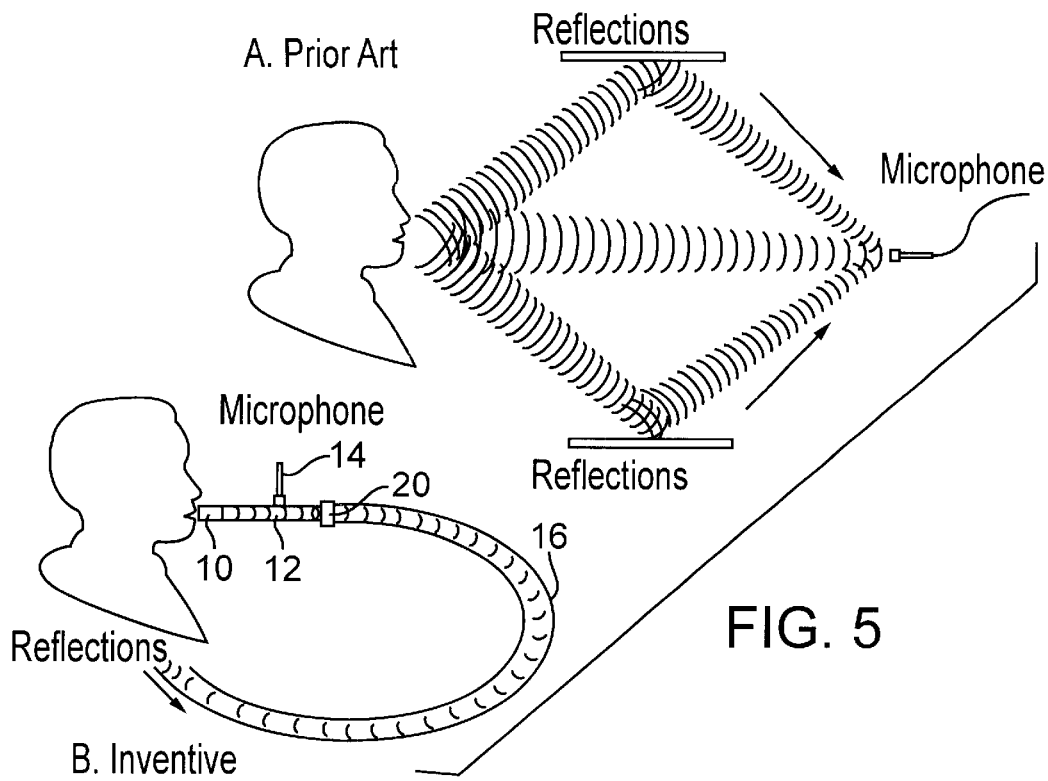
FIG. 5 illustrates two methods for measuring sound pressure waves. Panel A illustrates the interference in the recorded sound waves from reflections from the surrounding environment. Panel B illustrates the method of this invention which allows the interference to be essentially eliminated.

This invention provides a method and a system for analyzing cough sounds for diagnostic purposes. A diagram illustrating the present system to measure cough sounds is shown in FIG. 5B. A subject being tested coughs into a mouthpiece connected to a tube to which one or more microphones have been attached. The microphone is positioned so that its diaphragm is tangent to the inner surface of the tube and in a manner which minimizes reflections and/or distortion of sound waves passing through the tube. A long flexible section of hose or tubing is connected to the end of the metal tube opposite the mouthpiece. The system is designed so that the acoustical signal representing a cough sound pressure wave travels along the tube as a plane wave. As the sound travels through the long tubular system having a constant cross-section, it becomes attenuated. Any sounds reflected from the open tube back toward the microphone will be reduced in amplitude, therefore, and should not significantly interfere with cough sounds measured at the microphone. This can be compared with recording cough sounds in a room (FIG. 5A) in which reflections from the walls and objects in the room interfere with the recorded cough sounds. Moreover, further reflections are generated within the mouth as the sound waves passes from the mouth into the room with the system in FIG. 5A; since the cross sectional area dramatically increases (i.e., from the mouth to room), these reflections and/or distortions can be significant. The reflections from the walls, other objects and within the mouth itself are very difficult to eliminate. The present system significantly reduces and/or essentially eliminates such reflections or distortions. By using the essentially uniform cross section of the mouthpiece, rigid tubing, and flexible tubing, the reflections from wall or objects in the room are essentially eliminated. Moreover, since the mouthpiece and the mouth opening are essentially the same diameter when the subject coughs, reflections from this junction are also significantly reduced and minimized (especially relative to the situation illustrated in FIG. 5A).

Figure 6:
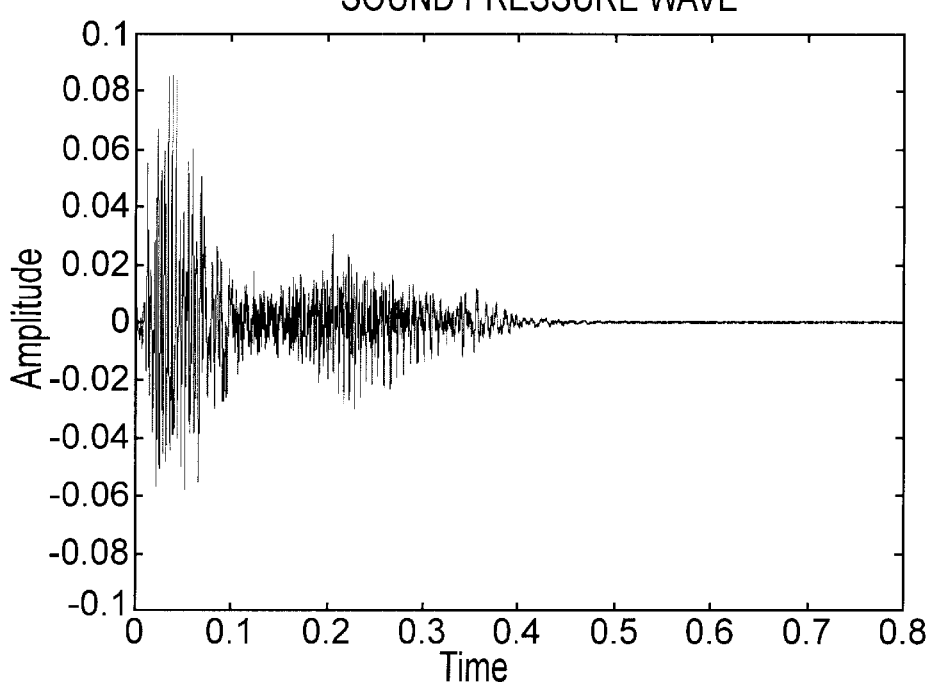
FIG. 6 illustrates a typical cough sound pressure wave generated using the apparatus and method of the present invention.
Figure 7:
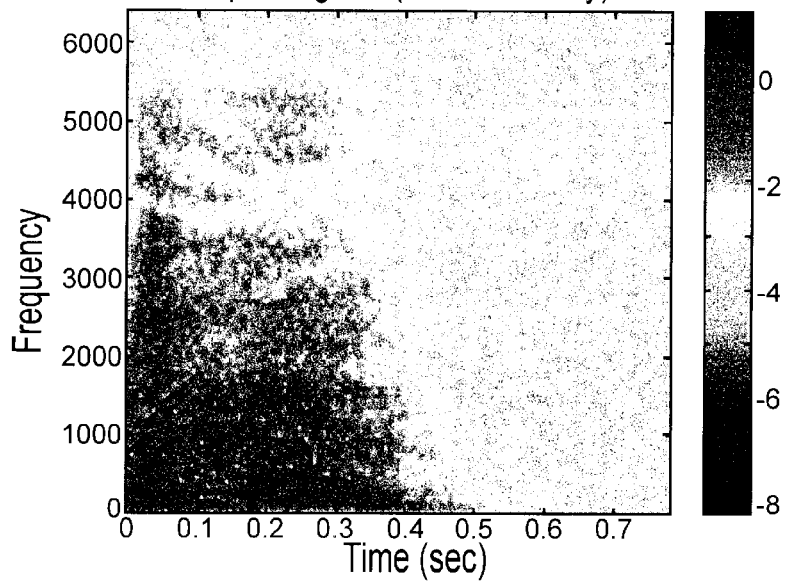
FIGS. 7 and 8 provide examples of spectrograms generated from the sound pressure wave of FIG. 6.
Figure 8:
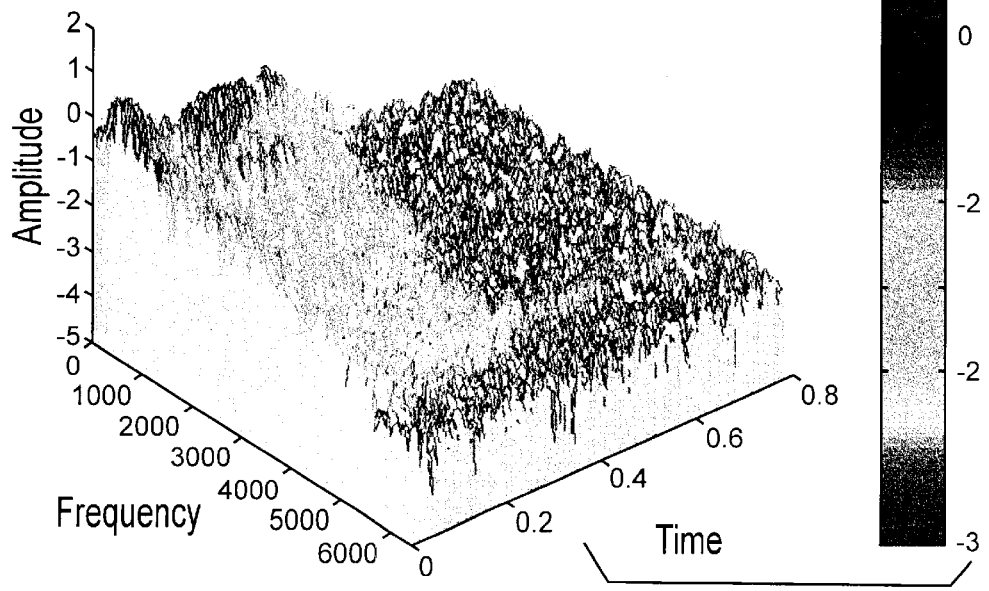

A sound pressure wave generated during a cough can be digitized and recorded using a sound analyzer. The digitized signal can then be transferred to a computer for analysis. An example of a cough sound pressure wave recorded with this system is shown in FIG. 6. The wave is complex and has many frequency components which change as a function of time. Since it is difficult to quantify differences between acoustical signals in the time domain by visual inspection only, spectrograms of the time signals have often been computed. Spectrograms show the frequency content of a signal versus time. An example showing the spectrogram of the sound pressure wave of the cough shown in FIG. 6 is shown in FIG. 7. The frequency content of the cough is plotted on the vertical axis versus time on the horizontal axis. The amplitude, or intensity, of individual frequency components of the cough are shown in terms of a logarithmic scale (shown by color) given on the right side of the Figure. The same information is plotted differently in FIG. 8 where the spectral intensity of the same cough is plotted on a logarithmic (DB) scale as a waterfall plot. Even though differences between coughs are more easily visualized with spectrograms, it still remains difficult to quantify the differences and likenesses between cough sounds from different sources.

Figure 9:
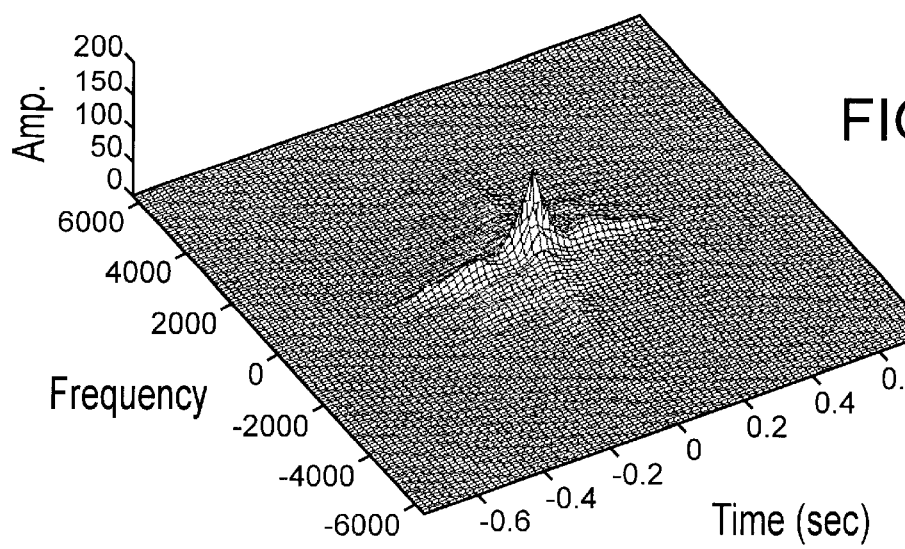
FIG. 9 illustrates a three dimensional autocorrelation plot of the data from FIG. 7.
Figure 10:
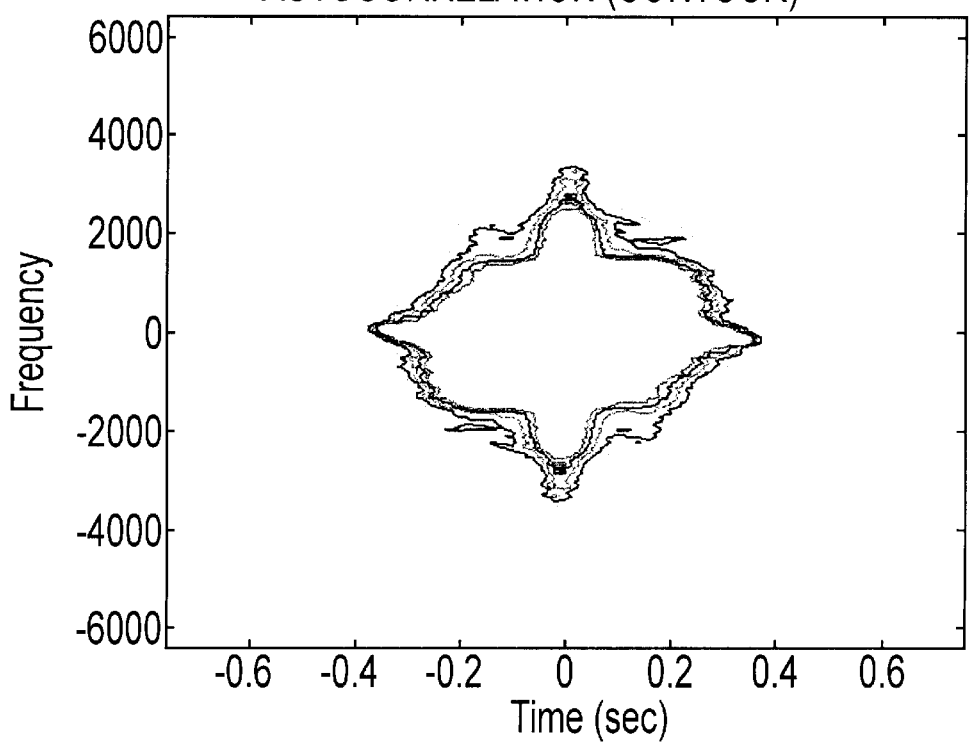
FIG. 10 shows the contour plot of the transitional region of the autocorrelation plot shown in FIG. 9 and corresponds to levels that are 1, 2, 3, 4, and 5 percent of the peak level. This contour plot illustrates the autocorrelation of a spectrogram obtained from a normal subject.
Figure 11:
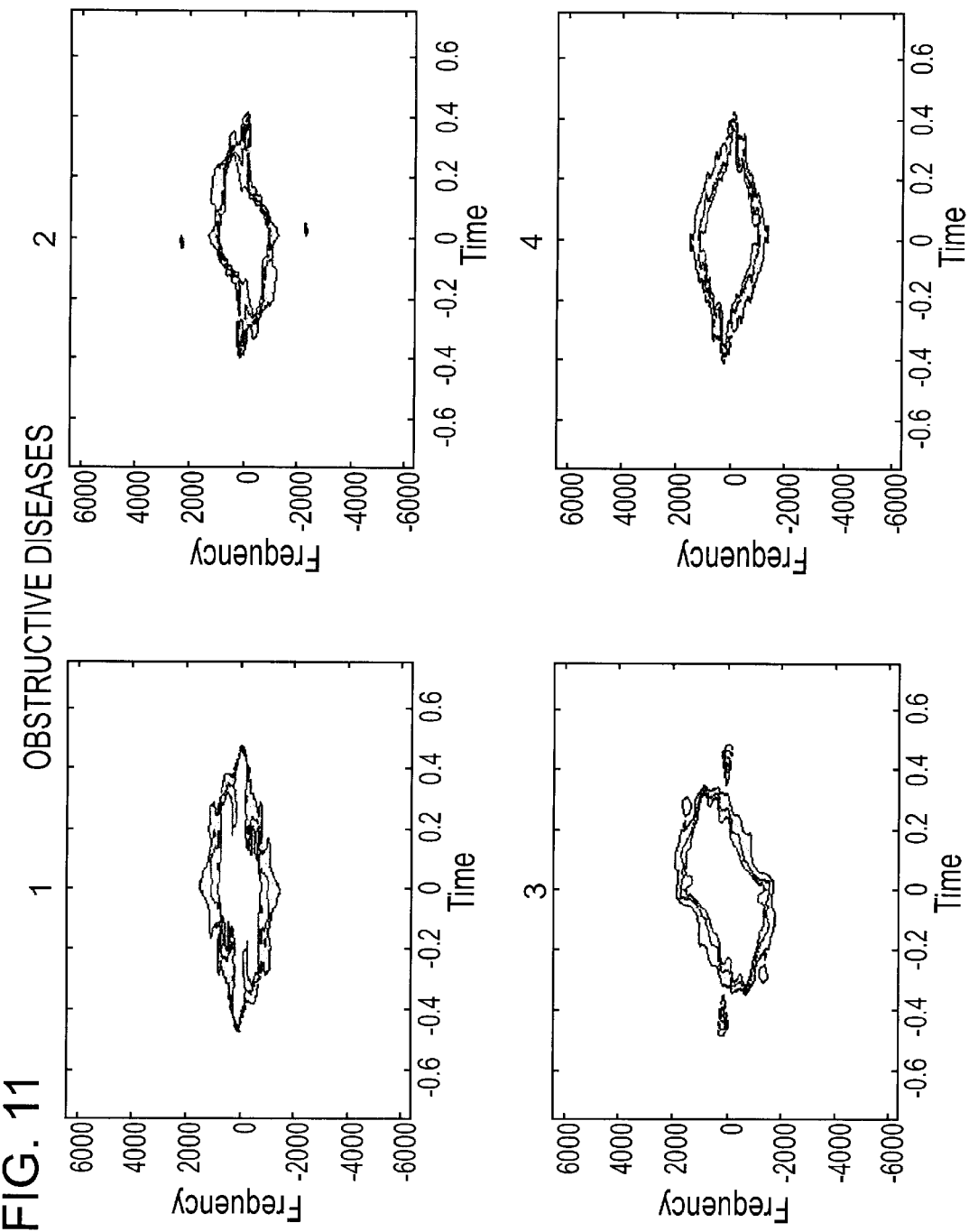
FIG. 11 provides contour plots similar to FIG. 10 from four patients diagnosed with obstructive lung diseases. The plots numbered 1 to 4 represent data from different patients.
Figure 12:
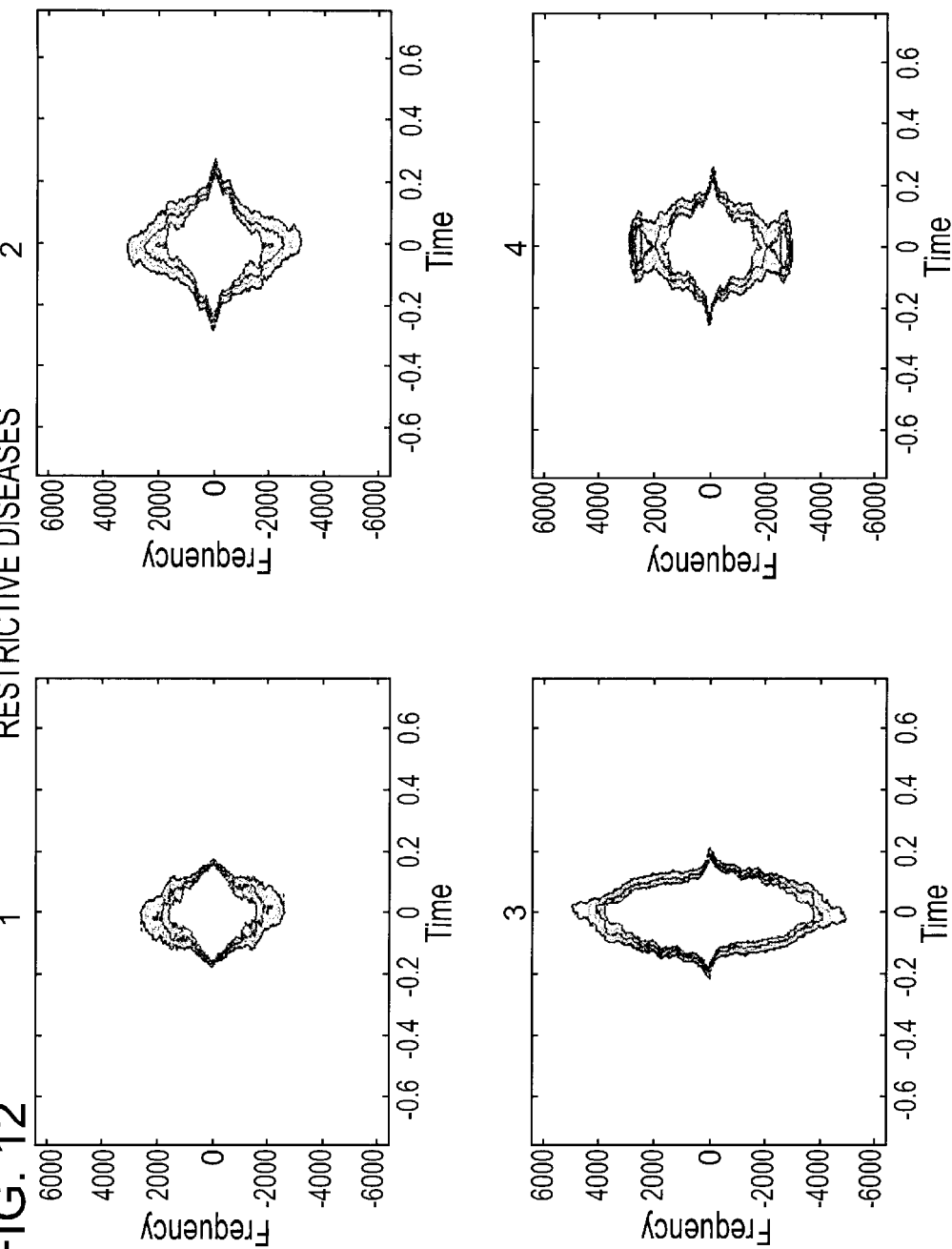
FIG. 12 provides contour plots similar to FIG. 10 from four patients diagnosed with restrictive lung diseases. The plots numbered 1 to 4 represent data from different patients.

A unique method to compare cough sounds would simultaneously compare how acoustical energy is distributed within a cough with respect to both time and frequency. An index, which uses a two dimensional autocorrelation function, describes how this information is distributed within a spectrogram image. The result is three dimensional autocorrelation image. An example of the normalized autocorrelation function of the spectrogram in FIG. 7 is shown in a mesh style plot in FIG. 9. The autocorrelation function forms a mountainous type surface with a peak at zero displacement (time($\tau$) and frequency($\omega$) are both zero). As $\tau$ and $\omega$ increase, the three dimensional mountainous surface approaches a plane surface. The mountain reflects regions in which the energy of the cough sound is located while the plains represent regions with little or no sound energy. The transitional region between the plain and the mountain is unique for each cough. The transitional region of the autocorrelation plot shown in FIG. 9 is shown as a contour plot in FIG. 10. This autocorrelation plot is for a normal or control cough. The contours shown correspond to levels that are 1, 2, 3, 4, and 5% of the peak level. The autocorrelation plot of the spectrogram of this normal subject forms a generally symmetrical surface in the horizontal and vertical directions. This normal or control contour plot can be compared with contour plots of the autocorrelation function of coughs from patients who are known to have obstructive lung disease (FIG. 11) and restrictive lung disease (FIG. 12).

The contour plots have different shapes for subjects having obstructive and restrictive lung diseases when compared to a healthy subject. In the case of obstructive lung disease, the plots are stretched out in the horizontal direction while remaining the same or decreasing in the vertical direction. In contrast, the plots from persons with restrictive lung disease are reduced in the horizontal direction while remaining the same or increasing in the vertical direction. Thus, the contour plots obtained from data produced by this invention provide a simplified method to diagnose lung disorders or diseases.

Figure 1:
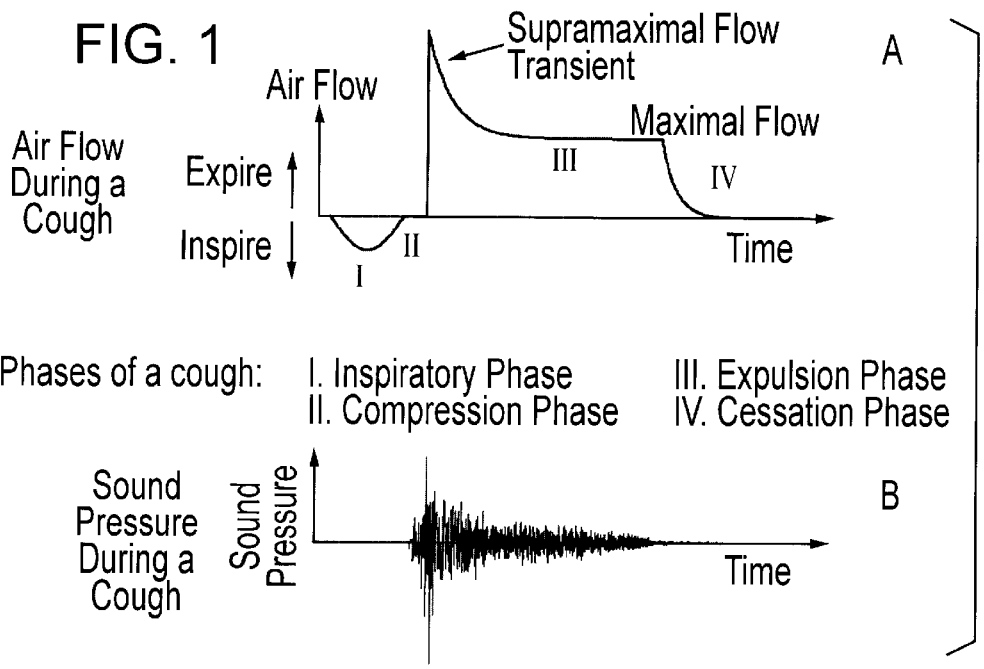
FIG. 1 illustrates the physical events during a typical cough (Panel A) and the sound pressure waves generated by such a typical cough (Panel B).
Figure 2:
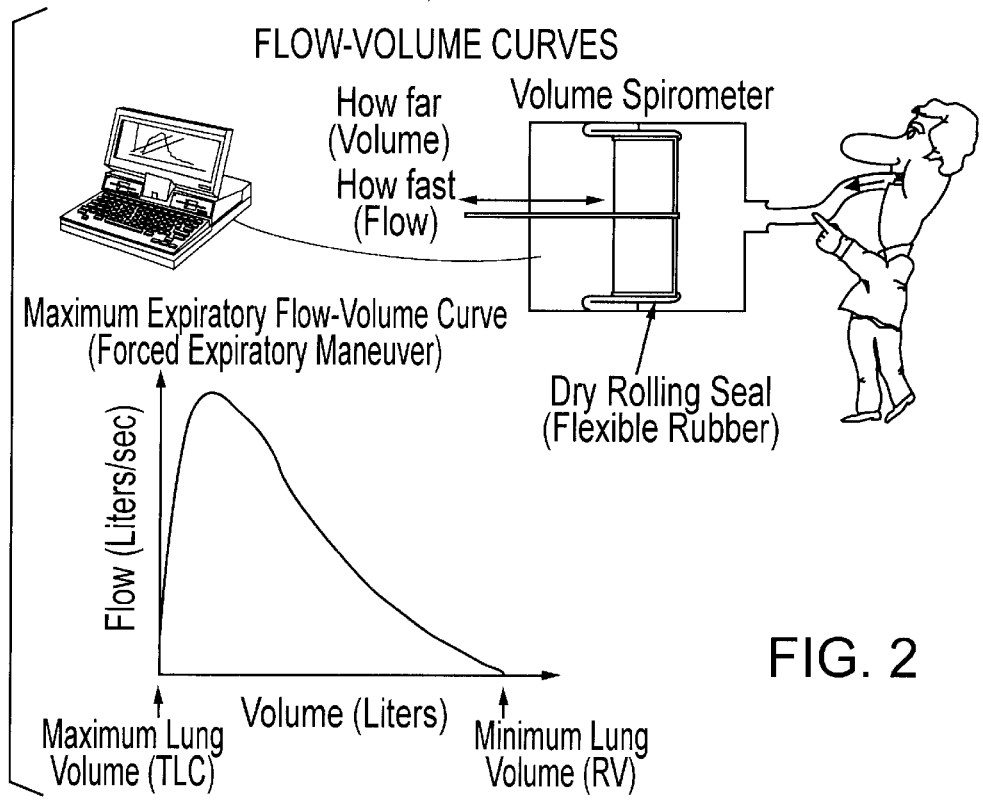
FIG. 2 provides an example of maximum expiratory flow volume (MEFV) curve with a patient expiring with maximum effort into a spirometer.
Figure 3:
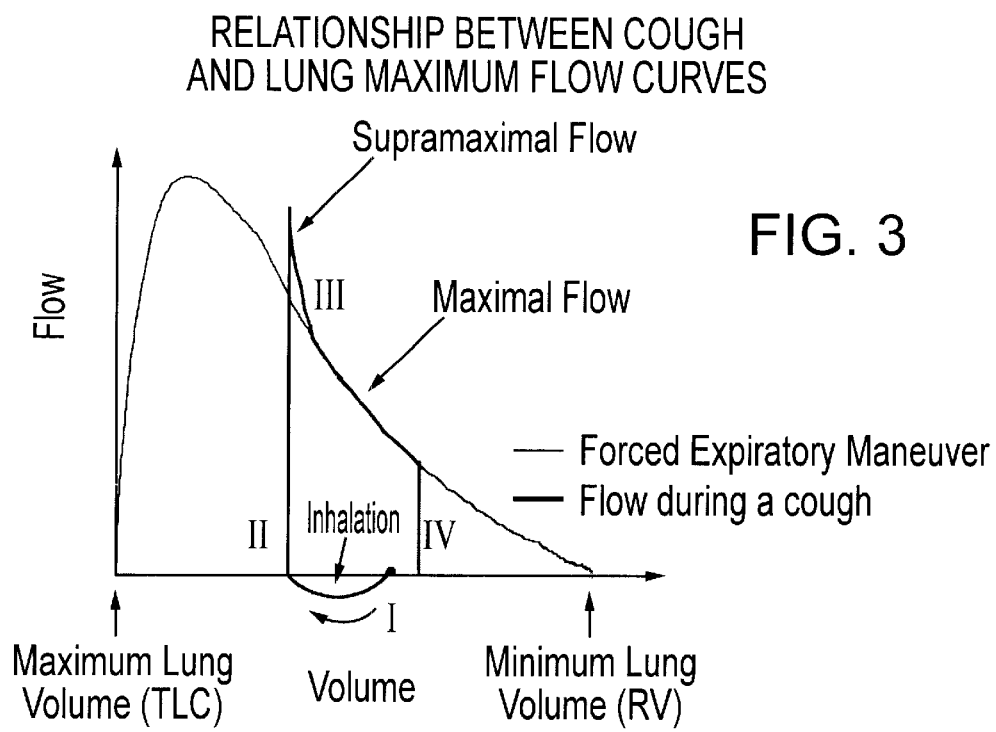
FIG. 3 illustrates the relationship of MEFV (FIG. 2) with the physical events of a typical cough (FIG. 1).
Figure 4:
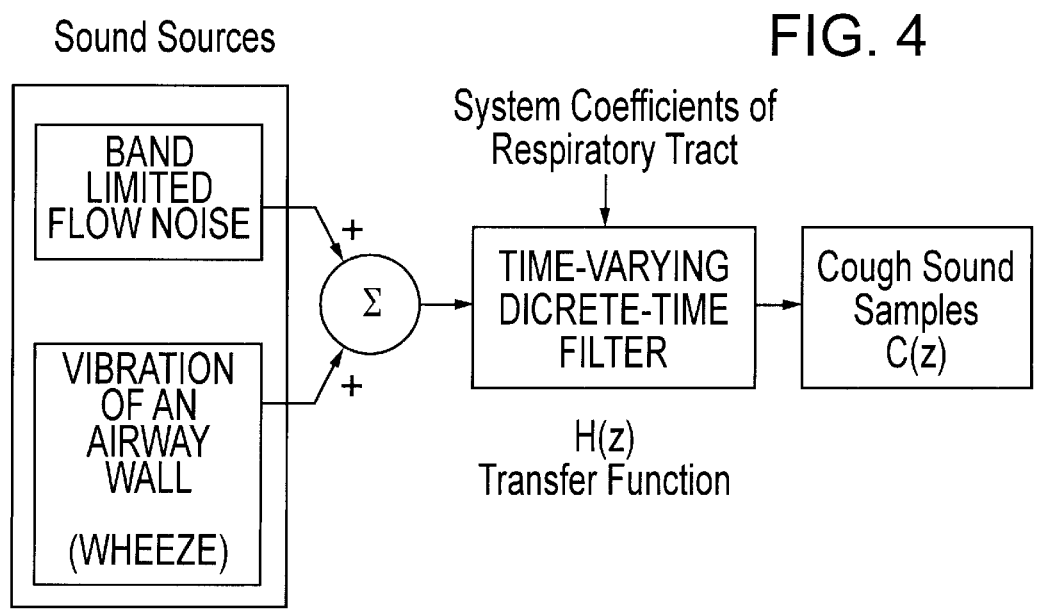
FIG. 4 provides a simple block diagram illustrating how typical cough sounds are produced.

In order to further simplify the analysis and provide a numerical estimation of pulmonary function, a cough sound index (CSI) or acoustic moment index was defined that was based on the shape of the transition contours of the autocorrelation of the spectrogram. This index was calculated using a moment analysis. Moments have often been used in the past to describe the shape characteristics of probability distribution functions (Kendel et al., The Advanced Theory of Statistics, Vol 1, Distribution Theory, New York, Hafner (1952)), the center of mass and the rotational properties of solid objects (Sears et al., "Rotation" in University Physics, Massachusetts, Addison-Wesley Publishing Company, Inc, Chapter 9, 157:180 (1956)) and even the analysis of the shape of flow volume curves of the lung (Becklake et al., "Evaluation of Tests of Lung Function for 'Screening' for Early Detection of Chronic Obstructive Lung Disease" in *The Lung in the Transition Between Health and Disease,* edited by P. T. Macklem and S. Permutt, New York and Basel, Marcel Decker, Chapter 16, 113–152 (1979)). Several moments of the autocorrelation of the spectrogram of a subject with obstructive lung disease illustrated in FIG. 11-1 have been calculated about the horizontal and vertical axis. The various equations of this moment analysis of the autocorrelation function, as well as specific values for the specific patient in FIG. 11-1 are as follows:

| Equations | Example (FIG. 11-1) |
|---|---|
| $0^{th}$ Moment (Area) | |
| $M_{x0} = \int f(x)dx$ | $M_{x0} = 0.0576$ |
| $M_{y0} = \int f(y)dy$ | $M_{y0} = 0.576$ |
| $1^{st}$ Moment (Mean) | |
| $M_{x1} = \int x \cdot f(x)dx$ | $M_{x1} = 0.520$ |
| $M_{y1} = \int y \cdot f(y)dy$ | $M_{y1} = 0.514$ |
| $2^{nd}$ Moment (Variance) | |
| $M_{x2} = \int (x - \bar{x})^2 \cdot f(x)dx$ | $M_{x2} = 0.00102$ |
| $M_{y2} = \int (y - \bar{y})^2 \cdot f(y)dy$ | $M_{y2} = 0.0000818$ |
| $3^{rd}$ Moment (Skewness) | |
| $M_{x3} = \int (x - \bar{x})^3 \cdot f(x)dx$ | $M_{x3} = 3.95 \times 10^{-7}$ |
| $M_{y3} = \int (y - \bar{y})^3 \cdot f(y)dy$ | $M_{y3} = 2.98 \times 10^{-10}$ |
| $4^{th}$ Moment (Kurtosis) | |
| $M_{x4} = \int (x - \bar{x})^4 \cdot f(x)dx$ | $M_{x4} = 2.28 \times 10^{-5}$ |
| $M_{y4} = \int (y - \bar{y})^4 \cdot f(y)dy$ | $M_{y4} = 2.64 \times 10^{-7}$ |

The second moment is used in the definition of the cough sound index (CSI). The second moment $M_{y2}$ is equivalent to the moment inertia of the autocorrelation about the horizontal axis and $M_{x2}$ is equivalent to the moment of inertia of the autocorrelation about the vertical axis. The CSI is calculated as follows:
(1) when $M_{x2}/M_{y2}<1$, then $$CSI=10\cdot[(M_{x2}/M_{y2})-1]$$

and (2) when $M_{x2}/M_{y2}\geq 1$, then $$CSI=(M_{x2}/M_{y2})-1$$

The CSI index tends to be large and positive for persons with obstructive lung disease and negative for persons with restrictive lung disease. Normal subjects should have a cough index near zero. In the case of the patient from FIG. 11-1, $M_{x2}/M_{y2}$ is 12.5 and, therefore, the CSI is 11.5, which indicated an obstructive lung disease in agreement with the clinical evaluation. The other moments indicated above could be used to further define the shape of the autocorrelation function and could also be used for diagnostic purposes.

Figure 13:
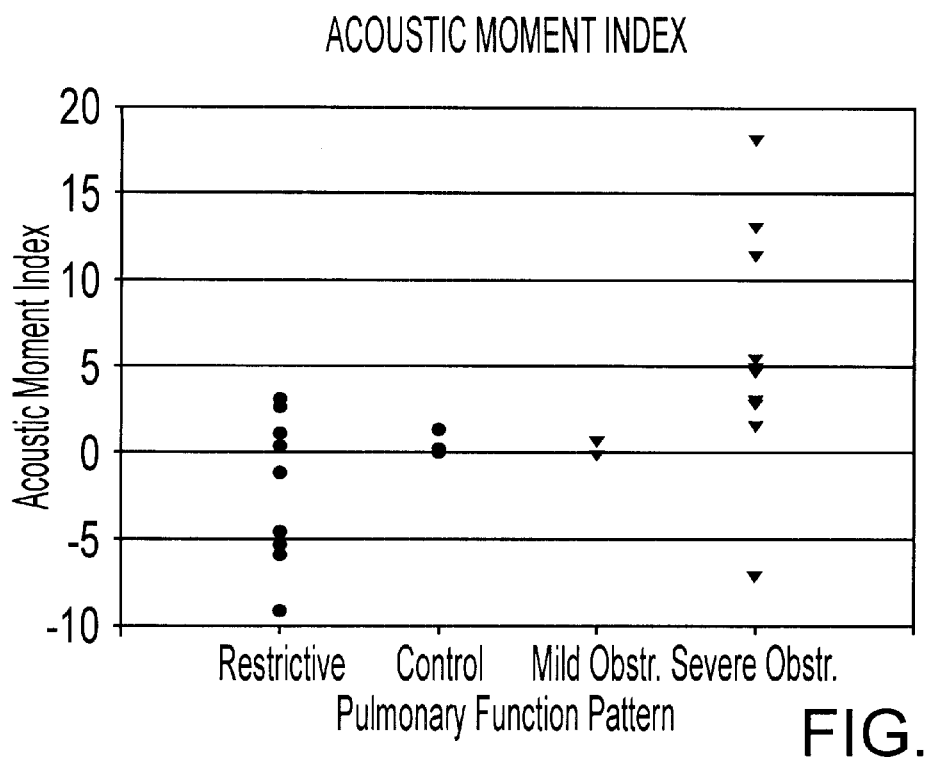
FIG. 13 plots the cough sound or acoustic moment index as determined by the present method for control patients (normal) and patients with impaired lung function.

Patients with obstructive and restrictive lung diseases who volunteered to have their cough sounds analyzed while being tested at the pulmonary clinic of the Department of Pulmonary Medicine at West Virginia University School of Medicine were tested. Their cough sound or acoustic moment indices were computed and compared with their clinical diagnosis based on spirometry measurements. The results are shown in FIG. 13. Although the statistical analysis has not been completed, this study shows good agreement between the clinical diagnosis and the diagnosis made using the cough sound index.

Figure 14:
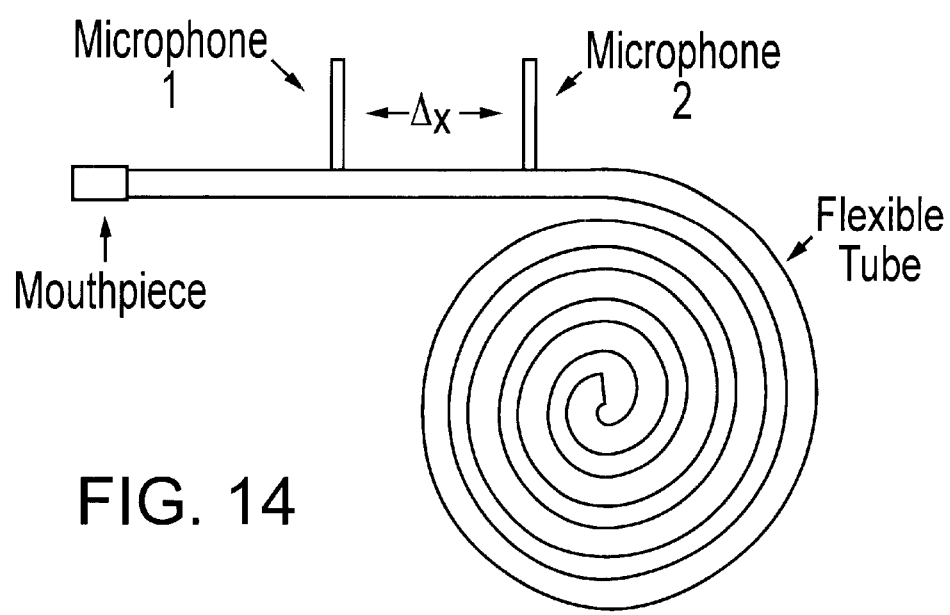
FIG. 14 illustrates a system of this invention for recording cough pressure waves using two microphones.
Figure 16:
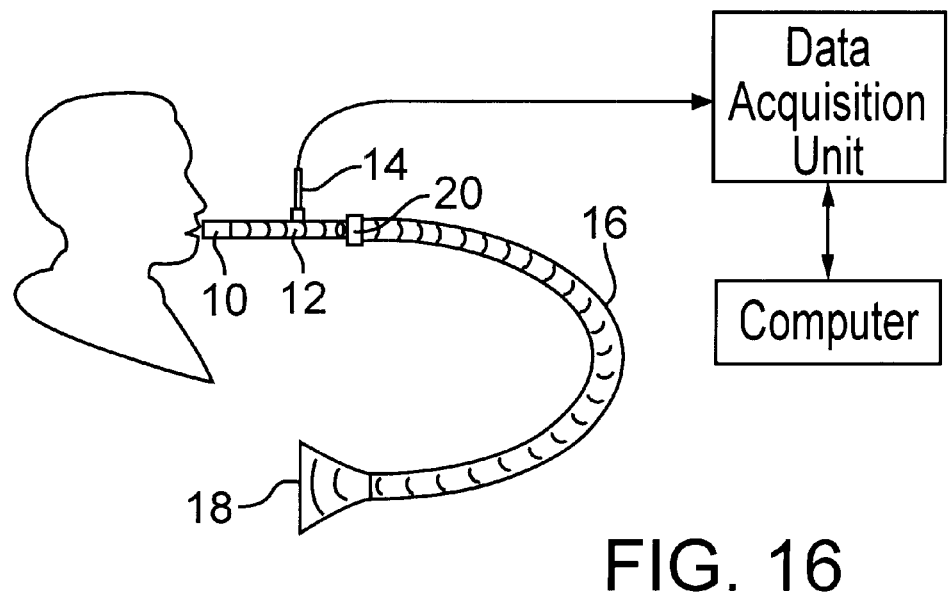
FIG. 16 illustrates the system of this invention showing the data acquisition system, computer, and an exponential horn for terminating the flexible tubing.

FIGS. 5B and 16 illustrates the present system using one microphone. A subject being tested coughs into a mouthpiece 10 connected to a tube 12 to which one or more microphones 14 have been attached. Preferably the mouthpiece 10 is adapted to fit the mouth of the patient; normally the mouthpiece has a diameter of about one inch. Preferably the mouthpiece 10 is disposable so that a new one can be used for each patient. Of course, other sized mouthpieces can also be used; for example, the mouthpiece could be in the range of about 0.5 to about 2 inches in diameter. (Indeed, for testing children, smaller diameter mouthpieces may be preferred; in such case, the other components should be modified to have the same diameter and cross-sectional area.) The mouthpiece 10 is attached to a tube 12 which is preferably rigid. The tube 12 is preferably constructed out of rigid plastic or metal and has a circular cross section without any tapering. Normally the inside diameter of tube 12 is comparable to that of mouthpiece 10. Thus, the inside diameter of tube 12 is preferably about one inch although it could vary from about 0.5 to about 2 inches in diameter. The mouthpiece 10 is attached to the proximal end of the tube 12. Generally the tube 12 is about 6 to 18 inches long; other lengths can be used if desired. A long flexible tube 16 is attached to the distal end of the tube 12 using coupling 20. Preferably, coupling or joint 20, as well as other joints within the system, are essentially "seamless" so as to minimize reflections as the sound waves pass the joints. Located between the proximal and distal ends of the tube 12 is the microphone 14. The microphone 14 is generally perpendicular to the tube such that its diaphragm is essentially tangential to, and essentially flush with, the inner surface of the tube. Preferably the microphone 14 is sufficiently small so that it does not significantly distort or interfere with the sound waves as they pass from the patient down the tube. A ¼ inch microphone (Bruel & Kjaer, Model 4136) has been found acceptable. As shown in FIG. 14, more than one microphone can be used if desired. Such a system may further limit the effect of reflections and/or other distortions.

Generally, the length of the flexible tube is adjusted so that (1) reflections of sound waves back toward the microphone are significantly reduced or minimized and (2) the back pressure or resistance within the tubing is not sufficient to significantly distort the cough. Generally the length of the flexible tubing 16 is about 2 to about 50 feet. More preferably, the length is about 10 to about 25 feet; for a inner diameter of about one inch, a length of about 15 feet appears to give reliable and reproducible results. The flexible tubing can be looped or coiled so long as it is not kinked or otherwise significantly distorted. Suitable materials for the flexible tubing include, for example, gum rubber, neoprene, hypalon, silicone, santoprene, tygon, latex, norprene, and the like. The flexible tubing 16 preferably has the same inside diameter and cross section (e.g., circular) as the tube 12. Preferably the joints or couplings (e.g., coupling 20) between the various components are essentially "seamless" to avoid distortions to the sound wave as it passes through the system. The distal end of the flexible tubing 16 is open. Preferably the distal end of the flexible tubing 16 is terminated with an anechoic termination (e.g., an exponential horn 18 as shown in FIG. 16)

The main function of the flexible tubing is to attenuate the sound signal in order to reduce reflections. After the "true" (i.e., reflection and distortion free) signal is expelled from the mouth it travels through the mouthpiece and is recorded by the microphone in the rigid tube. At this point, it would be ideal to effectively make the sound "disappear" so as to eliminate any reflections of the signal that could be picked up by the microphone. Such reflections would appear as noise in the recording and would be difficult to separate from the true signal. The flexible tubing provides an outlet for the sound to travel into and a means to attenuate the signal. Since the flexible tubing is approximately the same inside diameter as the rigid tube (along with the mouthpiece and mouth opening), the acoustic impedance mismatch is minimized, thereby significantly reducing reflections that might occur at the junction of the rigid tube and the flexible tube. As the sound travels down the flexible tube, part of the energy is absorbed by the tube, thereby attenuating the signal. The more the sound is attenuated the less signal remains which can be reflected. When the sound reaches the end of the tube, if open, there is a large cross-sectional area change (i.e., diameter of the tubing to size of room) which can cause a considerable reflection. To better match cross-sectional areas, the distal end of the flexible tube is terminated in an anechoic termination to further attenuate reflections. Thus, for example, an exponential horn 18 (e.g., trombone bell or horn) can be added at the distal end of the flexible tube as shown in FIG. 16. The portion of the signal that is reflected then travels back up the flexible tube (where it is further attenuated); any reflected signal remaining and which reaches the microphone will be recorded as unwanted noise on top of the signal. Theoretically, if the tube was long enough the reflected signal would not "come back" to the microphone until the recording period (i.e, normally one second) was over. This is not feasible, however, since substantially increasing the tubing length increases resistance to flow which can produce unnatural coughs. Thus, there is a tradeoff in noise reduction (i.e., reduction in reflected sound) and increased resistance. With inside diameters of about one inch throughout the system, a length of about 2 to about 50 feet is acceptable with a length of about 10 to about 25 feet being preferred, and a length of about 15 feet being most preferred.

Types of flexible tubing that are suitable for the present invention include, for example, gum rubber, neoprene, hypalon, silicone, santoprene, tygon, latex, norprene, and the like. The major factors affecting the different types of flexible tubing appears to be their sound absorbency and their "loading effects" (i.e., distortion of the signal due to the acoustical properties of the tubing itself). Thus, with each type of tubing there is a tradeoff between attenuation and loading. Latex tubing appears to give the greatest attenuation; tygon tubing appears to provide the least loading; and neoprene appears to provide the best combination of the two factors. The preferred tubing at the present time is, therefore, latex, tygon, and neoprene.

Figure 15:
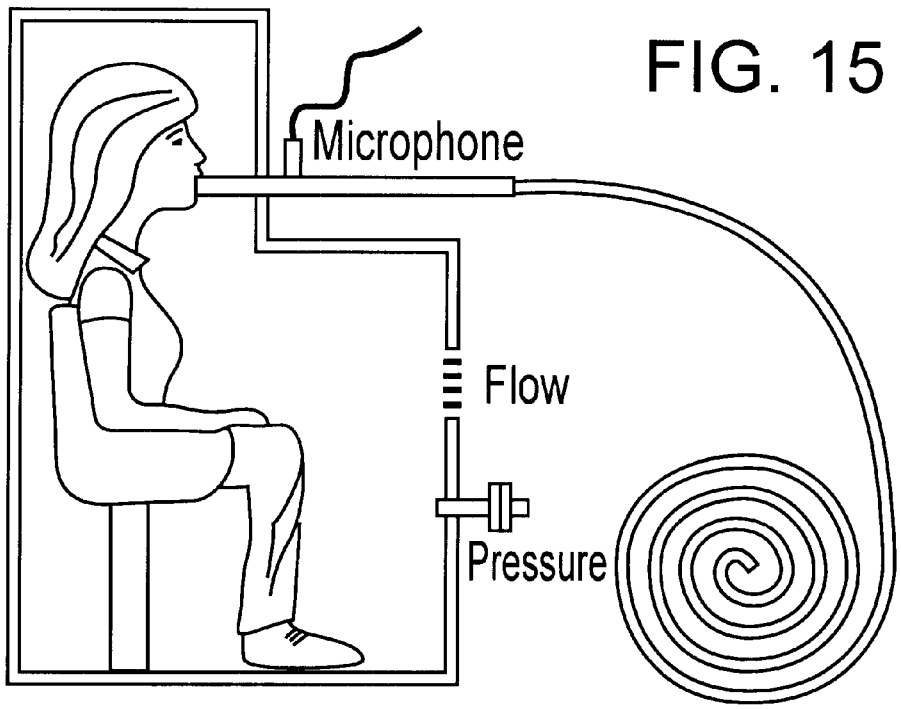
FIG. 15 illustrates the system of the present invention combined with a whole body plethsmorgraph.

The mouthpiece 10, tube 12, microphone 14, flexible tube 16, and coupling 20 are designed to minimize the distortion of the pressure waves moving through the system. Thus, they should be as closely matched as possible with regard to the inside diameter and cross sectional area to provide essentially seamless transitions. As discussed above, these components typically have an inside diameter of about 0.5 to 2 inches, preferably about 0.75 to 1.5 inches, and most preferably about 1 inch. The cross section throughout the system should be uniform and preferably is circular. Thus, the acoustical signal representing a cough sound pressure wave travels along the various components as a plane wave. As the sound travels through the long tubular system having a constant cross-section, it becomes attenuated. Any sounds reflected from the open tube back toward the microphone will be reduced in amplitude, therefore, and do not significantly interfere with cough sounds measured at the microphone. For comparison purposes, FIG. 5A illustrates recording cough sounds in a room in which reflections from the walls and objects in the room interfere with the recorded cough sounds. These reflections are very difficult to eliminate. The present system significantly reduces, and essentially eliminates, such reflections or distortions. The use of the exponential horn as shown in FIG. 16 can be, and preferably is, used to reduce the reflections and distortions even further. Additional attempts were made to modify the shape of the termination of the flexible tubing in order to even further reduce these reflection and distortions. For example, a conical wedge was placed at different locations within horn 18 in FIG. 16 to determine if distortions could be further reduced; the conical wedge had little or no effect. As shown in FIG. 15, the present system can also be used in conjunction with conventional plethysmograph techniques to measure lung volume. Thus, effects of lung volume on the cough sound index can be determined.

The following examples are intended to illustrate the invention and not to limit it. All references cited in this specification are hereby incorporated by reference. A computer software system was developed to assist in analyzing the sound pressure wave data. This software system, using the digitized sound pressure wave data, was used to generate the various spectrographs (FIGS. 7 and 8), the autocorrelation function (FIG. 9), the autocorrelation transition contour maps (FIGS. 10–12), and the cough sound index. The source code of this software system is included with this application as filed and is considered to be a part of this application and, therefore, is hereby incorporated by reference.

EXAMPLE 1

A cough analyzer as illustrated in FIG. 5B was constructed using a cylindrical mouthpiece attached to a one inch (i.d.) metal tube (eleven inches long). A ¼ inch microphone (Bruel & Kjaer, Model 4136) was mounted at 90° on the metal tube with its diaphragm tangent (i.e., flush) with the inner surface of the metal tube. A 15 foot section of flexible latex tubing was attached to the distal end of the tube. The flexible tubing was open at its distal end. Sound pressure waves from voluntary coughs were collected using the microphone and then digitized and recorded using a sound analyzer and computer. A five pole high pass Butterworth filter was applied to the data to reduce the effect of frequencies below about 50 Hz.

Cough sound measurements were obtained for 21 patients, including four controls; seven patients with restrictive lung disease, and 10 patients with obstructive lung disease based on conventional clinical examinations. Cough durations were defined as the time during which 0.05 to 99.95 percent of the cough energy occurred. The maximum energy frequency of the coughs was defined as the frequency where the maximum amount of energy occurred. The high frequency was the frequency below which 99.95 percent of the energy occurred during the cough. A cough sound index (CSI) was determined from the shape of the autocorrelation of the joint time-frequency spectrogram of the cough. The following results were obtained:

|  | Controls (n = 4) | Restrictive Lung Disease (n = 7) | Obstructive Lung Disease (n = 10) |
| --- | --- | --- | --- |
| Duration (msec) | 391 ± 44 | 369 ± 79 | 544 ± 51 |
| Maximum Energy Frequency (Hz) | 285 ± 24 | 212 ± 24 | 225 ± 29 |
| High Frequency (Hz) | 4428 ± 363 | 4052 ± 309 | 3821 ± 235 |
| CSI | −0.97 ± 1.30 | −1.37 ± 1.82 | 5.34 ± 1.97 |

Patterns were evident between the different disease types, especially when considering obstructive lung diseases.

EXAMPLE 2

Using equipment and procedures similar to Example 1, sound pressure waves from 25 volunteers (four controls; nine with restrictive lung disease; ten with marked obstructive lung disease; and two with mild obstructive lung disease) were obtained. A moment analysis of the contour representing a 97 percent decrease in the maximum value of the autocorrelation function was performed along both the $\Delta\tau$ and $\Delta\omega$ axes. The calculated second moments were used to determine the cough sound index (CSI). The following results were obtained:

| Subject | CSI |
| --- | --- |
| Controls | +0.08 ± 0.6 |
| Restriction | −2.11 ± 1.5 |
| Mild Obstruction | +0.31 ± 0.6 |
| Marked Obstruction | +5.85 ± 2.3 |

The results showed good agreement between cough sound analysis and clinical findings.

That which is claimed is:

1. An apparatus for recording and analyzing high fidelity cough sound measurements for use in diagnosing lung diseases or disorders, said apparatus comprising a mouthpiece, a tube having a distal end and a proximal end, a flexible tubing having a distal end and a proximal end, and a microphone; wherein the mouthpiece is attached to the proximal end of the tube, wherein the distal end of the tube is attached to the proximal end of the flexible tube, wherein the microphone is attached to the tube between its distal and proximal ends such that the microphone can record sound pressure waves within the system without distorting the sound pressure waves, and wherein the flexible tubing is sufficiently long so there are essentially no reflected sound pressure waves which interfere with the recording of the sound pressure waves at the microphone.

2. The apparatus as defined in claim 1 further comprising a sound analyzer for digitizing the sound pressure waves and a computer system to assist in analyzing the sound pressure waves.

3. The apparatus as defined in claim 1, wherein the microphone is attached perpendicular to the rigid tube and wherein the microphone has a diaphragm which is essentially tangential to, and essentially flush with, the inner surface of the rigid tube.

4. The apparatus as defined in claim 2, wherein the microphone is attached perpendicular to the rigid tube and wherein the microphone has a diaphragm which is essentially tangential to, and essentially flush with, the inner surface of the rigid tube.

5. The apparatus as defined in claim 1, wherein the flexible tubing is about 10 to about 25 feet long, wherein the mouthpiece, the rigid tube, and the flexible tubing each has a circular cross section and an inner diameter of about 0.5 to about 2 inches, and wherein the distal end of the flexible tubing is terminated with an anechoic termination.

6. The apparatus as defined in claim 2, wherein the flexible tubing is about 10 to about 25 feet long, wherein the mouthpiece, the rigid tube, and the flexible tubing each has a circular cross section and an inner diameter of about 0.5 to about 2 inches, and wherein the distal end of the flexible tubing is terminated with an anechoic termination.

7. The apparatus as defined in claim 3, wherein the flexible tubing is about 10 to about 25 feet long, wherein the mouthpiece, the rigid tube, and the flexible tubing each has a circular cross section and an inner diameter of about 0.5 to about 2 inches, and wherein the distal end of the flexible tubing is terminated with an anechoic termination.

8. The apparatus as defined in claim 4, wherein the flexible tubing is about 10 to about 25 feet long, wherein the mouthpiece, the rigid tube, and the flexible tubing each has a circular cross section and an inner diameter of about 0.5 to about 2 inches, and wherein the distal end of the flexible tubing is terminated with an anechoic termination.

9. The apparatus as defined in claim 2, wherein the apparatus can be used to generate (1) a spectrogram of the sound pressure waves; (2) an autocorrleation function of the spectrogram; and (3) a graphical representation of the transition contours of the autocorrelation function; wherein the graphical representation of the transition contours can be used to diagnose lung diseases or disorders.

10. The apparatus as defined in claim 8, wherein the apparatus can be used to generate (1) a spectrogram of the sound pressure waves; (2) an autocorrleation function of the spectrogram; and (3) a graphical representation of the transition contours of the autocorrelation function; wherein the graphical representation of the transition contours can be used to diagnose lung diseases or disorders.

11. The apparatus as defined in claim 2, wherein the apparatus can be used to generate (1) a spectrogram of the sound pressure waves; (2) an autocorrleation function of the spectrogram; (3) transition contours of the autocorrelation function; (4) second moments $M_{x2}$ and $M_{y2}$ from the transition contours; and (5) a cough sound index (CSI) wherein, if $(M_{x2}/M_{y2})$ is less than one, then $$CSI=[(M_{x2}/M_{y2})-1] \cdot 10$$

and, if $(M_{x2}/M_{y2})$ is greater than or equal to one, then $$CSI=[(M_{x2}/M_{y2})-1];$$

and wherein the cough sound index can be used to diagnose lung diseases or disorders.

12. The apparatus as defined in claim 8, wherein the apparatus can be used to generate (1) a spectrogram of the sound pressure waves; (2) an autocorrleation function of the spectrogram; (3) transition contours of the autocorrelation function; (4) second moments $M_{x2}$ and $M_{y2}$ from the transition contours; and (5) a cough sound index (CSI) wherein, if $(M_{x2}/M_{y2})$ is less than one, then $$CSI=[(M_{x2}/M_{y2})-1] \cdot 10$$

and, if $(M_{x2}/M_{y2})$ is greater than or equal to one, then $$CSI=[(M_{x2}/M_{y2})-1];$$

and wherein the cough sound index can be used to diagnose lung diseases or disorders.

13. A method for analyzing a patient's cough for diagnostic purposes, said method comprises (1) providing a system for analyzing coughs wherein the system comprises a mouthpiece, a tube having a distal end and a proximal end, a flexible tubing having a distal end and a proximal end, and a microphone; wherein the mouthpiece is attached to the proximal end of the tube, wherein the distal end of the tube is attached to the proximal end of the flexible tube, wherein the microphone is attached to the tube between its distal and proximal ends such that the microphone can record sound pressure waves within the system without distorting the pressure waves, and wherein the flexible tubing is sufficiently long so there are essentially no reflected sound pressure waves which interfere with the recording of the sound pressure waves at the microphone; (2) allowing the patient to cough into the mouthpiece; (3) recording the sound pressure waves generated by the patient's cough with the microphone; and (4) analyzing the recorded sound pressure waves.

14. The method as defined in claim 13, wherein the recorded sound pressure waves are digitized before being analyzed.

15. The method as defined in claim 14, wherein the recorded sound pressure waves are analyzed using spectrograms from which contour plots can be generated.

16. The method as defined in claim 15, wherein a sound analyzer is used for digitizing the sound pressure waves and a computer system is used to assist in analyzing the sound pressure waves.

17. The method as defined in claim 16, wherein the microphone is attached perpendicular to the rigid tube and wherein the microphone has a diaphragm which is essentially tangential to, and essentially flush with, the inner surface of the rigid tube.

18. The method as defined in claim 17, wherein the flexible tubing is about 10 to about 25 feet long, wherein the mouthpiece, the rigid tube, and the flexible tubing each has a circular cross section and an inner diameter of about 0.5 to about 2 inches, and wherein the distal end of the flexible tubing is terminated with an anechoic termination.

19. The method as defined in claim 18, wherein the mouthpiece, the rigid tube, and the flexible tubing each has an inner diameter of about 0.75 to about 1.5 inches.

20. The method as defined in claim 19, wherein the flexible tubing is about 15 feet long.

21. The method as defined in claim 16, wherein the spectrogram of the sound pressure waves is used to determine an autocorrleation function of the spectrogram; wherein a graphical representation of transition contours of the autocorrelation function is generated; and wherein the graphical representation of the transition contours can be used to diagnose lung diseases or disorders.

22. The method as defined in claim 17, wherein the spectrogram of the sound pressure waves is used to determine an autocorrleation function of the spectrogram; wherein a graphical representation of transition contours of the autocorrelation function is generated; and wherein the graphical representation of the transition contours can be used to diagnose lung diseases or disorders.

23. The method as defined in claim 18, wherein the spectrogram of the sound pressure waves is used to determine an autocorrleation function of the spectrogram; wherein a graphical representation of transition contours of the autocorrelation function is generated; and wherein the graphical representation of the transition contours can be used to diagnose lung diseases or disorders.

24. The method as defined in claim 16, wherein the spectrogram of the sound pressure waves is used to determine an autocorrleation function of the spectrogram; wherein transition contours of the autocorrelation function are determined; wherein second moments $M_{x2}$ and $M_{y2}$ are determined from the transition contours; and wherein a cough sound index (CSI) is determined, if $(M_{x2}/M_{y2})$ is less than one, from the equation $$CSI=[(M_{x2}/M_{y2})-1]\cdot 10$$

and, if $(M_{x2}/M_{y2})$ is greater than or equal to one, from the equation $$CSI=[(M_{x2}/M_{y2})-1];$$

and wherein the cough sound index can be used to diagnose lung diseases or disorders.

25. The method as defined in claim 17, wherein the spectrogram of the sound pressure waves is used to determine an autocorrleation function of the spectrogram; wherein transition contours of the autocorrelation function are determined; wherein second moments $M_{x2}$ and $M_{y2}$ are determined from the transition contours; and wherein a cough sound index (CSI) is determined, if $(M_{x2}/M_{y2})$ is less than one, from the equation $$CSI=[(M_{x2}/M_{y2})-1]\cdot 10$$

and, if $(M_{x2}/M_{y2})$ is greater than or equal to one, from the equation $$CSI=[(M_{x2}/M_{y2})-1];$$

and wherein the cough sound index can be used to diagnose lung diseases or disorders.

26. The method as defined in claim 18, wherein the spectrogram of the sound pressure waves is used to determine an autocorrleation function of the spectrogram; wherein transition contours of the autocorrelation function are determined; wherein second moments $M_{x2}$ and $M_{y2}$ are determined from the transition contours; and wherein a cough sound index (CSI) is determined, if $(M_{x2}/M_{y2})$ is less than one, from the equation $$CSI=[(M_{x2}/M_{y2})-1]\cdot 10$$

and, if $(M_{x2}/M_{y2})$ is greater than or equal to one, from the equation $$CSI=[(M_{x2}/M_{y2})-1]:$$

and wherein the cough sound index can be used to diagnose lung diseases or disorders.

* * * * *